US00PP20849P2

(12) United States Plant Patent
Vasquez Vargas

(10) Patent No.: US PP20,849 P2
(45) Date of Patent: Mar. 16, 2010

(54) ***DRACAENA* PLANT NAMED 'WHITNEY'**

(50) Latin Name: *Dracaena deremensis*
Varietal Denomination: WHITNEY

(75) Inventor: Juan Carlos Vasquez Vargas, Palmares, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 12/316,874

(22) Filed: Dec. 17, 2008

(51) Int. Cl.
*A01H 5/00* (2006.01)

(52) U.S. Cl. ..... Plt./383
(58) Field of Classification Search ..... Plt./383
See application file for complete search history.

*Primary Examiner*—Susan B McCormick Ewoldt
(74) *Attorney, Agent, or Firm*—Foley & Lardner LLP

(57) ABSTRACT

A new and distinct *Dracaena* plant named 'WHITNEY' particularly characterized by its distinctive light green and darker green variegated foliage streaks, longitudinally parallel to the leaf mid vein and more prominent surrounding leaf mid-rib (streaks same on front and back of leaf); leaves 35 cm to 45 cm in length; foliage that is slightly pendulous in overall shape; strong, thick stem; annual growth rate of 50 cm; and plant habit of a single stem ranging from 55 cm to 75 cm in width.

3 Drawing Sheets

Latin name of the genus and species of the claimed plant: *Dracaena deremensis.*

Variety denomination: 'WHITNEY'.

BACKGROUND OF THE INVENTION

The present invention relates to a new and distinct cultivar of *Dracaena* plant, botanically known as *Dracaena deremensis*, of the family Agavaceae, hereinafter referred to by the cultivar name 'WHITNEY'.

*Dracaena* is a monocotyledonous tropical foliage plant which can be produced as a single or multi-stemmed plant for interior use or outdoors in shade in zones 9 or 10 only.

The new *Dracaena* 'WHITNEY' originated from a naturally occurring branch mutation of the *Dracaena deremensis* cultivar designated 'Janet Craig' (unpatented). The new *Dracaena* 'WHITNEY' was discovered and selected by the inventor, Juan Carlos Vasquez Vargas, in June of 2004 as a single plant within the progeny of the stated mutation in a controlled environment in Palmares, Alajuela, Costa Rica.

Asexual reproduction of the new *Dracaena* cultivar by vegetative, air layer and rooted cuttings was first performed in June of 2004 in Palmares, Alajuela, Costa Rica, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'WHITNEY', which in combination distinguish this *Dracaena* as a new and distinct cultivar:

1. light green and darker green variegated foliage streaks, longitudinally parallel to the leaf mid vein and more prominent surrounding leaf mid-rib (streaks same on front and back of leaf);
2. Leaves 35 cm to 45 cm in length;
3. Foliage is slightly pendulous in overall shape;

4. Strong, thick stem;
5. Annual growth rate of 50 cm; and
6. Plant Habit: Single Stem ranges from 55 cm to 75 cm in width.

Plants of the new *Dracaena* 'WHITNEY' differ from plants of the parental cultivar, *Dracaena deremensis* 'Janet Craig' (unpatented) in the characteristics described in Table 1.

TABLE 1

| Characteristic | New Cultivar 'WHITNEY' | Parental Cultivar 'Janet Craig' (unpatented) |
|---|---|---|
| Leaf Color | Overall background, green, with variegated light green and darker green streaks | All green |
| Leaf thickness | Thicker, 1/64th inch | Thinner, 1/100th inch |
| Leaf texture | More leathery and more ribbed | Less leathery and less ribbed |
| Stem thickness | Thicker, 0.5 to 1.5 inch | Thinner, 0.25 to 1.25 inch |
| Stem Color | Greyed-Green Dark Streaks | Green |
| Internodes | Closer internodes at 0.5 inch | Further internodes at 1 inch |

Of the many commercial cultivars known to the present inventor, the most similar in comparison to the new *Dracaena* 'WHITNEY' is the parental cultivar, *Dracaena deremensis* 'Janet Craig' (unpatented), which is compared in Table 1 above.

BRIEF DESCRIPTION OF THE PHOTOGRAPHS

The accompanying photographs illustrate the overall appearance of the new *Dracaena* 'WHITNEY' showing the colors as true as is reasonably possible with colored reproductions of this type. Colors in the photographs may differ slightly from the color value cited in the detailed botanical description which accurately describe the color of 'WHITNEY'. The accompanying photographs show the distinctive light green and darker green variegated foliage streaks of a mature, typical plant of 'WHITNEY', following growth under appropriate growing conditions with colors being as true as possible with illustrations of this type.

DETAILED BOTANICAL DESCRIPTION

Figure 1:
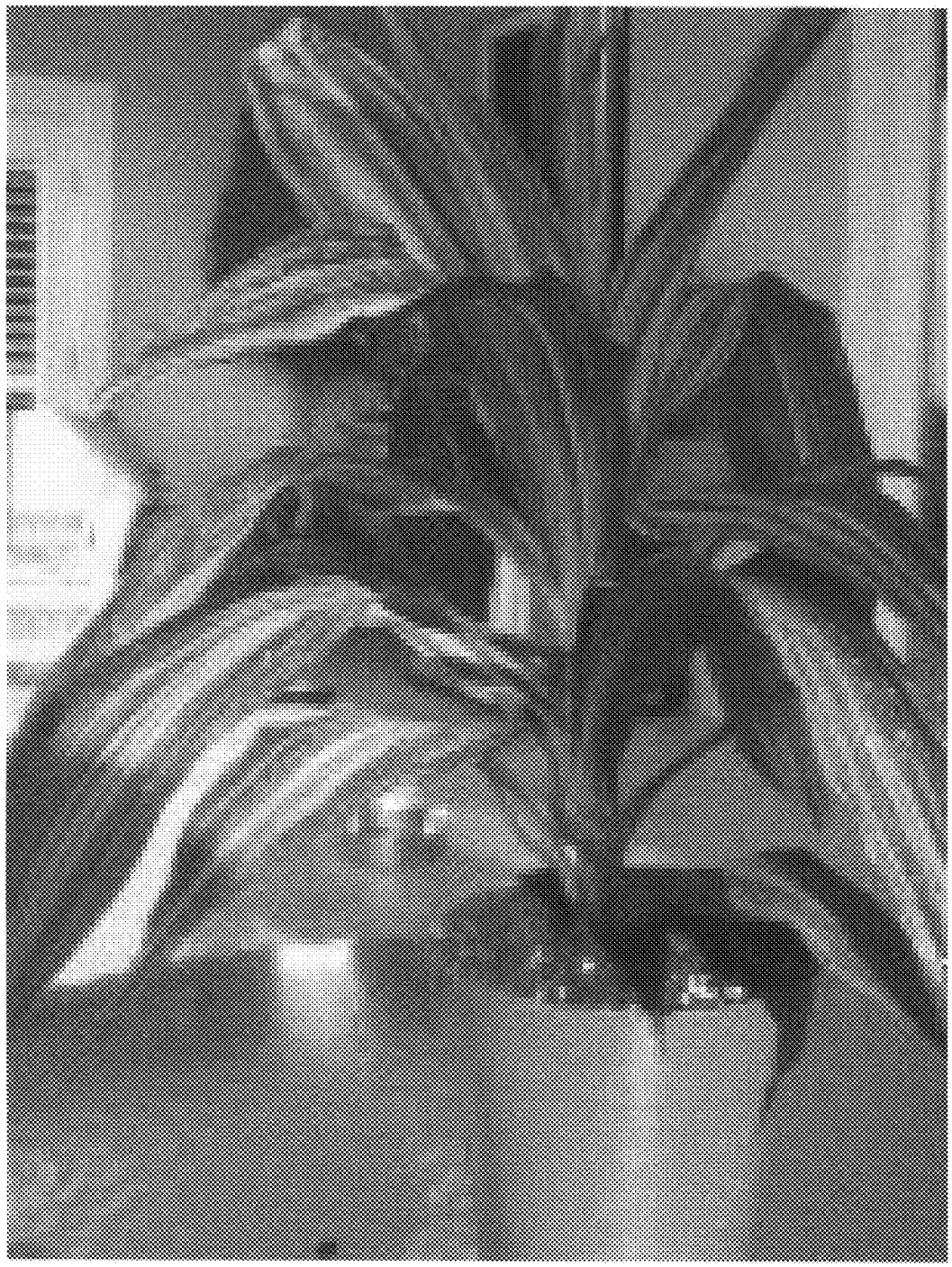
FIG. 1 shows a side view perspective a typical plant of 'WHITNEY' in a 26 cm pot, at 3 months of age.
Figure 2:
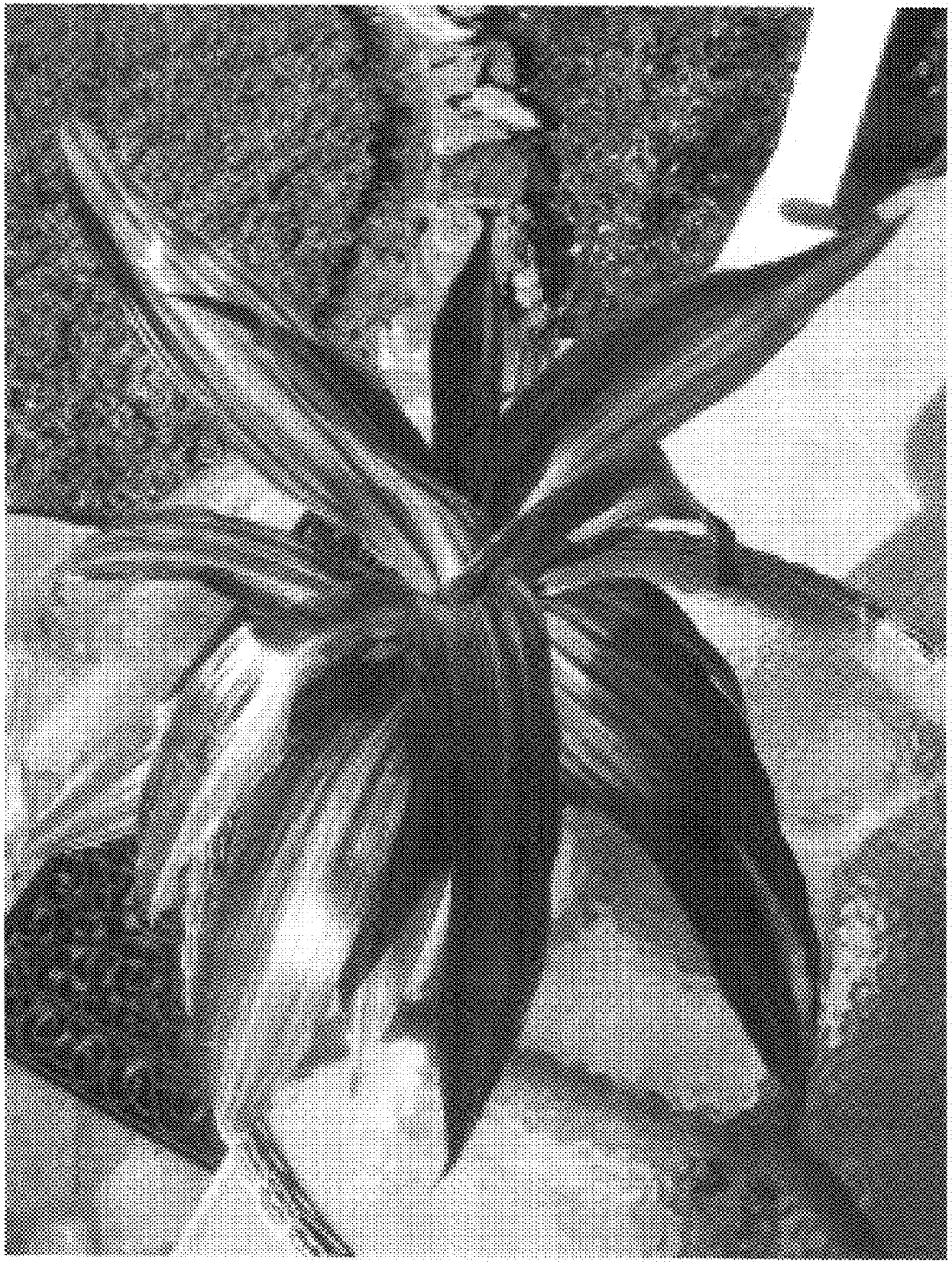
FIG. 2 shows a top view perspective a typical plant of 'WHITNEY' in a 26 cm pot, at 3 months of age.
Figure 3:
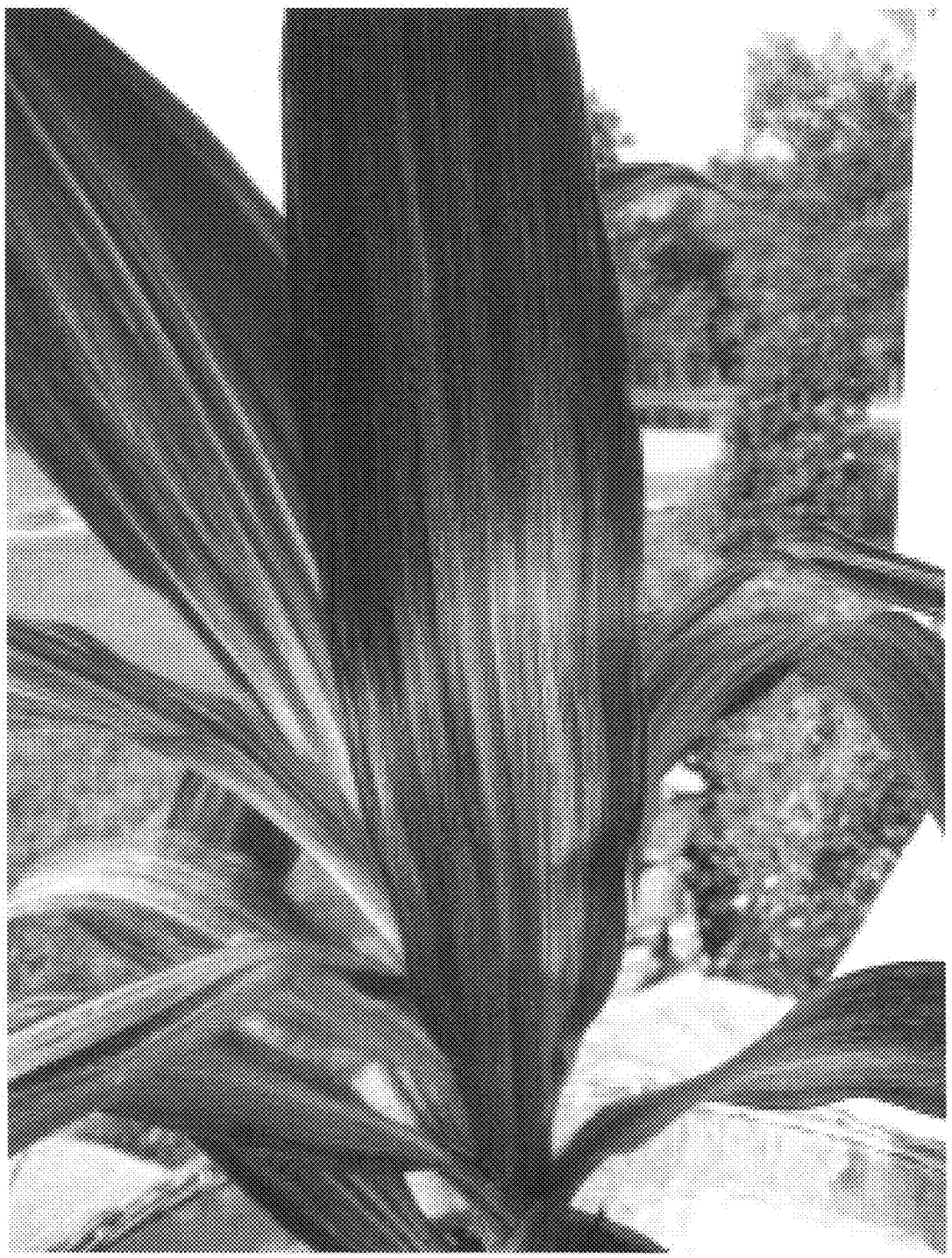
FIG. 3 shows a close-up view of the typical leaves of 'WHITNEY' at 3 months of age.

The new *Dracaena* 'WHITNEY' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dracaena* 'WHITNEY' as grown in greenhouses in Apopka, Fla., under conditions which closely approximate those generally used in commercial practice: (1) average day temperature of 90° F. and average night temperature of 70° F.; (2) light conditions of 80% shade from natural sunlight, (3) 80% relative humidity; (4) liquid feed 24-8-16 fertilizer applied weekly, and every 160 days, granular Nutricote 18-6-12 fertilizer is applied; and (5) no growth retardants used.

Color references are made to The Royal Horticultural Society Colour, Chart (R.H.S.), (2001 edition), except where general colors of ordinary significance are used. The photographs and descriptions were taken during the fall season in Apopka, Fla., when outdoor day temperatures averaged 85° F. and outdoor night temperatures averaged 70° F. The age of the plants described is 3 months, after planting from rooted cuttings.

Classification:

*Botanical.*—*Dracaena deremensis.*

Parentage: *Dracaena deremensis* 'Janet Craig' (unpatented).

Optimal growth conditions:

*Light intensities.*—80% shade.

*Temperature.*—Day: 75° F. to 95° F. Night: 65° F. to 75° F.

*Temperature tolerance.*—Tolerant to a low temperature of about 50° F. and tolerant to a high temperature of about 100° F.

*Fertilization.*—A balanced fertilizer with level of 24-18-16.

*Growth regulators.*—None.

Propagation:

*Type.*—Vegetative, by air layer or rooted cuttings.

*Rooting habit and description.*—Easy to root. Roots are mostly fibrous and slightly aromatic. New, emerging roots are white, RHS 155D, and mature roots are yellow-orange, RHS 22A.

*Time to initiate roots.*—About 10 to 15 days at 80° F.

*Time to produce a rooted cutting.*—About 30 to 45 days at 80° F.

Plant:

*General appearance and form.*—

*Height.*—About 300 cm when grown in ground; About 185 cm when grown in a 35 cm size container.

*Spread.*—About 65 cm to 90 cm (single stem) when grown in ground, About 55 cm to 75 cm when grown in 35 cm size container.

*Form.*—Monocot; leaves whorled, leaf bases wrap around the stem.

*Shape.*—Round.

*Growth rate and habit.*—About 50 cm annually; upright.

*Fragrance.*—None.

*Stem.*—Quantity per plant: About 3 per 26 cm container; about 4 per 35 cm container. Length: About 300 cm when grown in ground; About 185 cm when grown in 35 cm size container. Diameter: About 2 cm to 4 cm. Shape: Cylindrical. Texture: Thick (waxy and rubbery)and Ribbed. Color: Greyed-green, closest to RHS 194B and RHS 194C, with darker streaks of green, RHS 139D. Strength: Strong. Internode length: About 1 cm to 2 cm.

Foliage:

*Quantity.*—About 25 leaves per stem at 80 cm.

*Arrangement and attachment.*—Single, alternate; leaves whorled; leaf bases wrap around the stem.

*Leaf length.*—About 35 cm to 45 cm.

*Leaf width.*—About 6 cm to 10 cm.

*Overall shape of leaf.*—Slightly pendulous.

*Apex shape.*—Lanceolate.

*Base shape.*—Sheathing.

*Margin.*—Entire, slightly undulate, acuminate leaf rolled ½ cm at apex.

*Texture.*—Upper and Lower Surfaces: Leathery, longitudinally ribbed, lustrous.

*Pubescence.*—None.

*Mature leaf color.*—Upper and Lower Surfaces Overall background is Green, RHS 139A. Variegated streaks are light green, closest to green-white groups, RHS 157A and RHS 157B, and variegated streaks are more prominent surrounding leaf midrib, and then finer at outer half of leaf blade, and extend distance of stem and stem clasp.

*Immature leaf color.*—Upper and Lower Surfaces: Overall background is Green, RHS 139A. Variegated streaks are white, closes to white group, RHS 155A and RHS 155B, and variegates streaks are more prominent surrounding leaf midrib, and then finer at outer half of leaf blade, and extend distance from stem and stem clasp.

*Venation.*—Pattern: Several longitudinally, variegated streaks parallel the leaf veins. Mature leaf: Upper and Lower Surfaces: Variegated streaks are light green, closest to green-white groups, RHS 157A and RHS 157B. Immature leaf: Upper and Lower Surfaces: Variegated streaks are white, closes to white group, RHS 155A and RHS 155B.

*Leaf fragrance.*—None.

Inflorescence description: 'WHITNEY' may produce an inconspicuous raceme, inflorescence once annually in optimum growing conditions. Flower would be borne at apical meristem and emerge from leaf whorl at the top of the plant as in similar *Dracaena* species. At this time, no inflorescence of 'WHITNEY' has been observed.

Reproductive organs: No reproductive organs observed.

Disease/pest resistance: Typical to *Dracaena* species, no special observations made.

Disease/pest susceptibility: Typical to *Dracaena* species, no special observations made.

I claim:

1. A new and distinct *Dracaena* plant named 'WHITNEY', substantially as illustrated and described herein.

* * * * *